United States Patent [19]

Gezari

[11] 4,281,665
[45] Aug. 4, 1981

[54] THERMODILUTION INJECTION SYSTEM INCLUDING AN INJECTATE COOLING SYSTEM

[75] Inventor: Walter A. Gezari, Killingworth, Conn.

[73] Assignee: C. R. Bard, Inc., Murray Hill, N.J.

[21] Appl. No.: 25,923

[22] Filed: Apr. 2, 1979

[51] Int. Cl.³ .............................................. A61B 5/02
[52] U.S. Cl. .................................. 128/713; 128/655; 128/692
[58] Field of Search ............................. 128/654–658, 128/692, 713, 218 A, 255, 401; 73/204

[56] References Cited
U.S. PATENT DOCUMENTS

| | | | |
|---|---|---|---|
| 368,767 | 8/1887 | Heller | 128/401 |
| 1,723,738 | 8/1929 | Lang | 128/401 X |
| 3,155,090 | 11/1964 | Holter | 128/655 |
| 3,293,868 | 12/1966 | Gonzalez | 128/401 X |
| 3,460,538 | 8/1969 | Armstrong | 128/401 |
| 3,604,263 | 9/1971 | Auphan et al. | 73/204 |
| 3,915,155 | 10/1975 | Jacobson et al. | 128/692 |
| 4,111,209 | 9/1978 | Wolvek et al. | 128/401 |
| 4,122,850 | 10/1978 | Bucalo | 128/255 |

Primary Examiner—Kyle L. Howell
Attorney, Agent, or Firm—Fishman and Van Kirk

[57] ABSTRACT

A thermodilution injection system comprising a syringe for delivering a measured amount of injectate in an accurately predetermined time period, and an injectate cooling device positioned in serial relation to the syringe for cooling the injectate when it is dispensed from the syringe.

9 Claims, 4 Drawing Figures

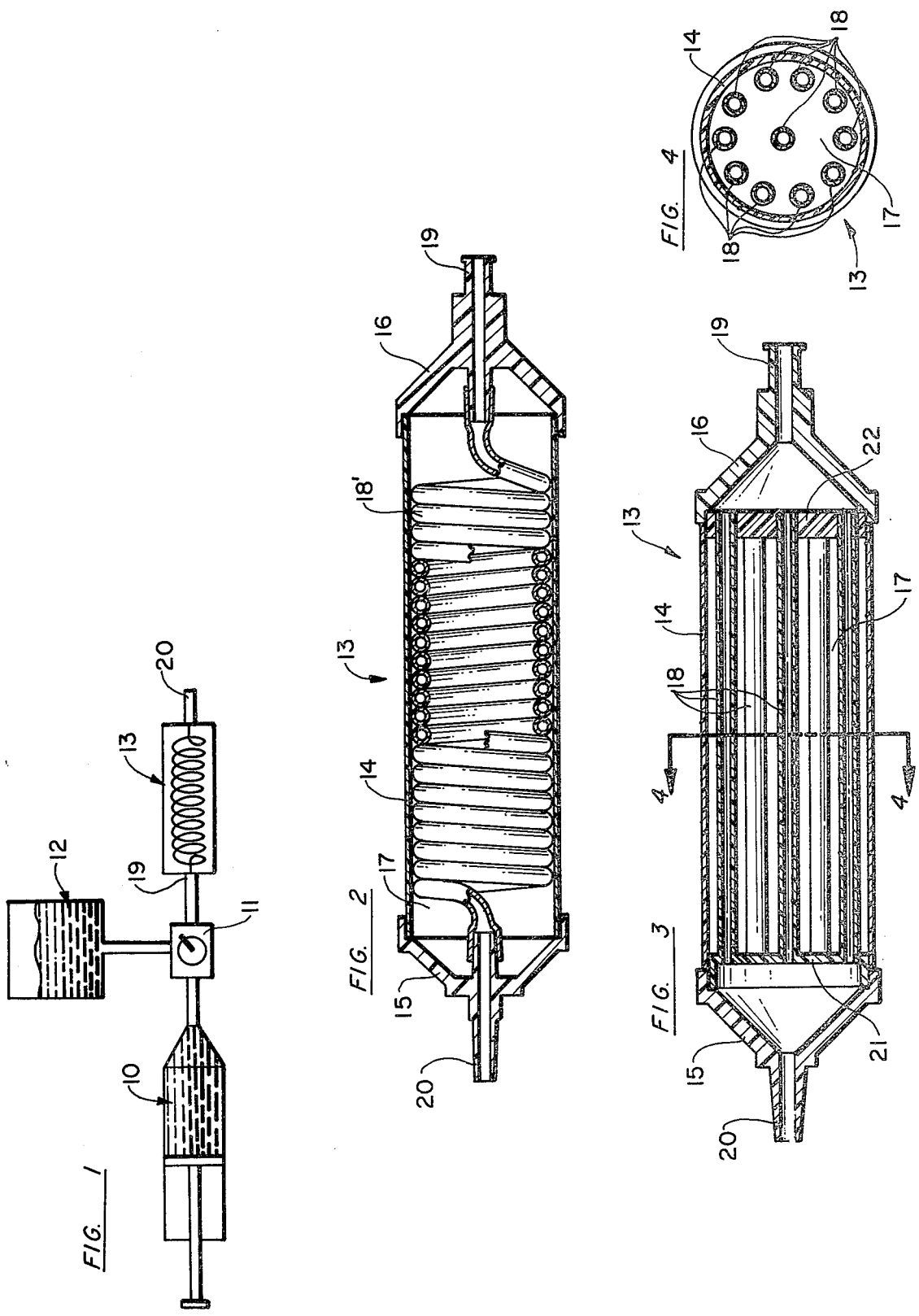

THERMODILUTION INJECTION SYSTEM INCLUDING AN INJECTATE COOLING SYSTEM

BACKGROUND OF THE INVENTION (1) Field of the Invention

The present invention relates to the determination of cardiac output of a patient by injecting a measured amount of cold injectate into the right heart proximal to the pulmonary artery in a predetermined time of short duration. More specifically, this invention is directed to a thermodilution injector including a syringe and an associated injectate cooling device and, more particularly, an injectate cooler for use in a thermodilution injector. Accordingly, the general objects of the present invention are to provide novel and improved methods and apparatus of such character.

(2) Description of the Prior Art

A well known test for the determination of cardiac output involves the injection of a measured amount of cold injectate solution into the right heart proximal to the pulmonary artery in a predetermined time period of short duration, such as, on the order of two seconds. The temperature drop of the blood passing a thermistor positioned in the heart is then sensed and measured. The decrease in blood temperature in a given time resulting from the cold injectate solution, when integrated by a cardiac output computer, is a measure of the output capacity of the heart in liters per minute. This technique for determining cardiac output is well known and is of considerable importance in diagnosing and treating critically ill patients. The value of the technique of thermodilution cardiac output monitoring is directly related to the accuracy of the process. Many thermodilution cardiac output computers are commercially available for obtaining determinations of cardiac output from a blood temperature drop curve.

The reliability of the technique of thermodilution cardiac output monitoring depends on the accuracy and the repeatability of the injection process. It has been found to be difficult to provide a predetermined amount of injectate having a predetermined cold temperature on a repeatable basis. In order for the output readings to be accurate, repeatable and reliable, the injectate must have a predefined constant temperature and must be delivered to the patient over a short predetermined period of time, which must be the same for each injection. If the temperature of the injectate varies, the rate of change of blood temperature over a given time will also vary, and the computer output readings will thus be inaccurate and unreliable. Bearing in mind that injection should occur over a time period of approximately two seconds, the time it takes for 10 cc of dextrose solution to be injected manually, it can readily be seen that a variation of only two degrees centigrade in temperature of the injectate can lead to substantial errors in measurement.

In the present method of thermodilution injection, a doctor or medical technician operates a syringe to deliver the injectate into a catheter placed in the right heart proximal to the pulmonary artery. The injectate is typically stored in a bottle which is positioned in an ice bath. Injectate having a temperature of 0° C. is delivered to the syringe. During transference of the injectate to the syringe and during the time in which the injectate remains in the syringe, the temperature of the injectate may increase. Moreover, the apparatus for cooling the injectate is cumbersome and difficult to operate. Since the cooled injectate must be transferred to the syringe, there exists a possibility of contamination of the injectate during transfer.

SUMMARY OF THE INVENTION

The thermodilution injection system of the present invention provides for the injection of an injectate having a relatively constant temperature, that is, a temperature of about 0° C. The thermodilution injection system includes a syringe for delivering a predetermined amount of injectate at a predetermined rate. An injectate cooling device is positioned in series relation to the syringe and downstream of the syringe. The injectate cooling device comprises a casing defining a fluid chamber, the casing preferably being formed of cylindrical tubular plastic. The chamber is bridged by one or a plurality of injectate flow conduits; the conduit or conduits typically being coaxial with the casing. In a preferred embodiment the injectate may flow between the opposite ends of a cylindrical casing via a plurality of parallel tubes which are individually exposed about their peripheries to a fluid within the casing. In accordance with another embodiment, a length of flexible tubular conduit is coiled through the chamber. The conduit or plural tubes have a predetermined volume, preferably 10.0 cc. The interior of the chamber is filled with a heat transfer liquid; i.e., a coolant; such as a mixture of water and isopropyl alcohol. Prior to use, the injectate cooling device is exposed to a cold environment such as that in a freezer and the liquid in the chamber is frozen. At this point in time, there is no fluid in the injectate flow path or paths.

The thus cooled injectate cooling device is connected in series relation to a syringe of the type having a displacement volume approximately equal to the volume within the parallel tubes or the coiled conduit of the injectate cooler, that is, about 10 cc. The liquid in the syringe is injected into the injectate cooler. The injectate is maintained within the cooling device for a time sufficient to reduce the temperature of the injectate to 0° C. The syringe is reloaded by withdrawing the syringe piston and aspirating additional liquid into the displacement chamber of the syringe. More detailed information concerning the syringe and the manner by which a measured amount of injectate in an accurately predetermined time period is delivered to the injectate cooler is set forth in copending U.S. Pat. Application Ser. No. 843,333 filed Oct. 20, 1977.

Once the syringe is filled with an additional volume of injectate, the volume of injectate in the cooling device may be injected into the heart. When the plunger of the syringe is moved forward, a volume of fluid is displaced and forced into the injectate cooler. The relatively warm fluid from the syringe displaces cold fluid in the injectate cooler and this cold fluid is forced from the injectate cooler into the heart via a conventional catheter.

The syringe can be filled with additional injectate and the above-described process of injecting the injectate into the heart can be repeated. Of course, the injectate cooling device should be replaced if the temperature of the liquid and ice in the chamber is no longer sufficient to cool the injectate to the desired temperature.

BRIEF DESCRIPTION OF THE DRAWING

The present invention may be better understood and its numerous objects and advantages will become apparent to those skilled in the art by reference to the accompanying drawing wherein like reference numerals refer to like elements in the several figures and in which:

FIG. 1 is a schematic diagram of a thermodilution injection system including an injectate cooling device;

FIG. 2 is a cross-sectional side elevation view of a preferred embodiment of an injectate cooling device in accordance with the present invention;

FIG. 3 is a cross-section end view, taken along line 3—3, of the apparatus of FIG. 2; and FIG. 4 is a sectional view of an alternative injectate cooling device as represented schematically.

DETAILED DESCRIPTION OF THE INVENTION

Referring to FIG. 1, the thermodilution injection system is shown. The system comprises a syringe 10 having a defined displacement volume, preferably a volume of at least 10.0 cc. The syringe is connected in series with a stop cock mechanism 11 having at least two positions. In one position, stop cock 11 provides for fluid communication between syringe 10 and reservoir 12. In the second position of stop cock 11, syringe 10 is in fluid communication with injectate cooling device 13. The outlet of injectate cooling device 13 is connected to a catheter which directs the injectate into the heart.

Referring jointly to FIGS. 3 and 4, an injectate cooling device in accordance with a preferred embodiment of the present invention comprises housing 14, typically of hollow cylindrical form, which receives first and second end caps 15 and 16. The housing 14 and end caps 15 and 16 define a chamber 17. This chamber is bridged by a plurality of parallel tubes 18. The interiors of tubes 18 are in fluid communication with an inlet port 19 which is integral with end cap 16. Tubes 18 are also in fluid communication with a discharge port 20 which is integral with end cap 15. The tubes 18 will normally be integral with a support plate 21. Tubes 18 will also pass through and be supported by apertured plate 22. Plates 21 and 22 will be sized to be received within the cylindrical housing 14. This subassembly comprising tubes 18 and plates 21 and 22 will be comprised of a material having suitable heat transfer characteristics. The end caps 15 and 16 will hold the subassembly comprising tubes 18 in position within housing 14 and will prevent leakage of coolant from the interior of housing 14. Chamber 17 will be filled with a coolant such as, for example, water mixed with 10% isopropyl alcohol. The volume between inlet port 19 and discharge port 20 will preferably be equal to the volume of the chamber in syringe 10.

Referring now to FIG. 2, a second embodiment of an injectate cooling device 13 in accordance with the present invention also comprises a cylindrical housing 14 provided with first and second end caps respectively indicated at 15 and 16. The housing 14 and end caps 15 and 16 define chamber 17 which receives the heat transfer fluid. In the FIG. 2 embodiment the parallel tubes 18 are replaced by a single injectate flow path in the form of a spiraled tube 18'. A first end of spiral tube 18' is in fluid communication with inlet port 19 while the opposite end of tube 18' is in fluid communication with the discharge port 20. As in the embodiment of FIGS. 3 and 4, the chamber 17 of the FIG. 2 embodiment is preferably filled with coolant and the volume of spiral tube 18' will be equal to the volume of the displacement chamber in syringe 10.

The injectate cooling device 13 may be sterilized and placed in a sterile package such as a hermetically sealed plastic bag. The bag is placed in a freezer and the liquid in chamber 17 is frozen. In order to use the injectate cooler, the cooling device 13 is connected in series relation with syringe 10 via stop cock 11. At this point in time, the dextrose and water solution in reservoir 12 will not have been injected into injectate cooling device 13. Stop cock 11 is moved to a position wherein syringe 10 is in fluid communication with reservoir 12. The piston of the syringe 10 is withdrawn to aspirate fluid from the reservoir into the displacement chamber of syringe 10. Stop cock 11 is then turned to a position wherein syringe 10 is in fluid communication with injectate cooling device 13. The piston of syringe 10 is moved forward to displace the dextrose and water solution into the injectate cooling device 13. Stop cock 11 is then moved back to the position wherein the syringe 10 is once again filled by withdrawing the piston and aspirating the dextrose solution into syringe 10. The stop cock 11 is then again moved to a position wherein syringe 10 is in fluid communication with injectate cooling device 13. The thermodilution injection system is now in a position to inject the dextrose solution. It should be understood that the dextrose solution has remained within injectate cooling device 13 for a sufficient period of time to cool the injectate solution to the desired temperature of, for example, 0° C. The time in which the injectate must remain within the injectate cooling device 13 in order for the injectate to reach the requisite temperature is dependent on the volume of the fluid in the tubes 18 or in the coiled conduit 18', the materials employed, the length of tubes 18 or conduit 18' and the heat transfer capability of the coolant fluid in chamber 17.

The plunger of syringe 10 may be operated by the thermodilution injector described in copending U.S. Patent Application Ser. No. 848,333 filed Oct. 20, 1977. The apparatus described in Application Ser. No. 848,333 operates the plunger of the syringe to deliver a measured amount of injectate in an accurately predetermined time period. Thus, the thermodilution injection process is made even more accurate by the use of the injectate cooling device which provides for the injection of a solution having a predetermined temperature.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. In a thermodilution injection system of the type including means for delivering a measured volume of cooled injectate into a patient's circulatory system through a catheter at predetermined time intervals, the improvement comprising:

housing means, said housing means being tubular in shape, said housing means have first and second ends, said first and said second ends being open, said housing means defining a cavity;

non-disposable conduit means, said conduit means being received by and partially filling said housing means cavity, said conduit means having first and second ends, said conduit means defining at least one injectate fluid passageway from said housing means first end to said housing means second end, said conduit means absorbing heat from the injectate, said conduit means having a volume commensurate ate with the measured volume of injectate supplied by the delivering means, said conduit means being sterilizable;

first cap means, said first cap means being received by and sealing said housing means first end, said first cap means being provided with a fluid port, said first cap means fluid port having first and second ends, said first cap means fluid port defining a fluid passageway for the injectate, said first cap means fluid port first end being in fluid communication with and sealed to said conduit means first end, said first cap means fluid port second end being in fluid communication with the delivering means;

second cap means, said second cap means being received by and sealing said housing means second end, said second cap means being provided with a fluid port, said second cap means fluid port having first and second ends, said second cap means fluid port defining a fluid passageway for the injectate, said second cap means fluid port first end being in fluid communication with and sealed to said conduit means second end, said second cap means fluid port second end being in direct fluid communication with and sealed to the catheter; and a liquid filling the remainder of said housing means cavity, the temperature of said liquid being capable of being reduced below the desired temperature of the injectate whereby said liquid will absorb heat from said conduit means and thereby cool the injectate to the desired temperature.

2. An apparatus according to claim 1 wherein said means for delivering a measured volume of injectate at predetermined time intervals comprises a syringe having a predetermined displacement volume and wherein said conduit means has a volume equal to said measured volume.

3. The improved apparatus of claim 1 wherein said conduit means comprises a spiral tube.

4. An apparatus according to claim 3 wherein said means for delivering a measured volume of injectate in a predetermined time period comprises a syringe having a predetermined displacement volume and wherein said conduit means has a volume equal to said predetermined volume.

5. An apparatus according to claim 4 further comprising a reservoir for the injectate and valve means for selectively placing said syringe in fluid communication with said reservoir and said first cap means fluid port.

6. Improved apparatus of claim 1 wherein said conduit means comprises a plurality of substantially parallel tubes and means for placing opposite ends of said tubes respectively in fluid contact with and sealed to said fluid port first end of said first cap means and said fluid port first end of said second cap means.

7. An apparatus according to claim 6 wherein said means for delivering a measured volume of injectate in a predetermined time period comprises a syringe having a predetermined displacement volume and wherein said conduit means has a volume equal to said predetermined volume.

8. An apparatus according to claim 7 further comprising a reservoir for the injectate and valve means for selectively placing said syringe in fluid communication with said reservoir and said first cap means fluid port.

9. The improved apparatus of claim 6 wherein said means for placing said ends of said tubes in fluid contact with said respective cap means fluid port first ends comprises:

first sealing wall means, said wall means engaging said first ends of said tubes, said wall means defining a cavity with said first cap means, said wall means sealing said fluid medium means within said housing cavity; and second sealing wall means, said wall means engaging said second ends of said tubes, said wall means defining a cavity with said second cap means, said wall means sealing said fluid medium means within said housing means cavity.

* * * * *